United States Patent [19]

Bergman

[11] Patent Number: 5,501,955
[45] Date of Patent: Mar. 26, 1996

[54] IMMUNOLOGICAL TEST FOR THE PRESENCE OF ANTIBODIES IN BIOLOGICAL FLUIDS

[75] Inventor: Andreas Bergman, Berlin, Germany

[73] Assignee: B.R.A.H.M.S. Diagnostica GmbH, Berlin, Germany

[21] Appl. No.: 971,822

[22] PCT Filed: Jun. 15, 1992

[86] PCT No.: PCT/EP92/01348

§ 371 Date: Apr. 20, 1993

§ 102(e) Date: Apr. 20, 1993

[87] PCT Pub. No.: WO93/00587

PCT Pub. Date: Jan. 7, 1993

[30]     Foreign Application Priority Data

Jun. 20, 1991 [DE] Germany .................... 41 20 412.3

[51] Int. Cl.$^6$ .................... G01N 33/564; G01N 33/543
[52] U.S. Cl. .................... 435/7.93; 435/7.92; 435/7.94; 435/7.95; 435/28; 436/503; 436/506; 436/518
[58] Field of Search .................... 435/7.4, 7.92, 435/7.93, 7.94, 7.95, 28; 436/503, 506, 518, 523, 524, 528, 538, 811

[56]            References Cited

PUBLICATIONS

Harlow et al, 1988. *Antibodies. A Laboratory Manual.* Cold Spring Harbor Laboratory, Cold Spring Harbor pp. 567–569, 579–583, 591.

Ruf et al, 1988. Novel routine assay of thyroperoxidase autoantibodies. Clin Chem 34:2231–34.

Schardt et al, 1982 An enzyme–linked immunoassay for thyroid microsomal antibodies. J Immunol Meth 55:155–68.

Ruf et al, 1989. Relationship between immunological structure and biochemical properties of human thyroid peroxidase. Endocrinol. 125:1211–18.

Seradyn, Inc., 1988. Microparticle immunoassay techniques. Seradyn, Inc. pp. 4, 26–27.

Oellerich, 1984. Enzyme–immunoassay. A review. J Clin Chem Clin Biochem 22:895–904.

*Primary Examiner*—Toni R. Scheiner
*Assistant Examiner*—James L. Grun
*Attorney, Agent, or Firm*—Cushman Darby & Cushman

[57]            ABSTRACT

Antibodies (Ak), in particular autoantibodies, such as autoantibodies against thyroid peroxidase (TPO), are determined by a procedure in which the sample to be investigated is reacted with two further, in particular monoclonal antibodies and an antigen. The two further antibodies are an immobilised antibody ($Ak_{imm}$) and a freely labelled antibody (Ak*) against the antigen (Ag), and the latter is preferably used in the form of a crude, natural antigen, for example in the form of an organ extract. The presence of the antibodies (Ak) to be determined is evident as a disturbance of the formation of a sandwich of the two added antibodies ($Ak_{imm}$ and Ak*) with the added antigen (Ag) and as a consequent reduction in the binding of the label to the solid phase.

12 Claims, 3 Drawing Sheets

IMMUNOLOGICAL TEST FOR THE PRESENCE OF ANTIBODIES IN BIOLOGICAL FLUIDS

The invention relates to an immunological assay method for the determination of antibodies in biological fluids, in particular of autoantibodies, the detection of which permits the diagnosis of an autoimmune disease.

Various immunological assay methods play a very important role in medical diagnostics. In addition to those assay methods aimed at the qualitative and/or quantitative determination of antigens or haptens, for example hormones, there are also many assay methods of this type for the determination of antibodies in biological fluids, in particular human sera.

Antibodies are proteins which are designated as immunoglobulins (Ig) and which are formed by the body as a reaction to an antigen. Since antigens normally have many antigenic determinants, antibodies are polyclonal and therefore represent a population of proteins having different binding properties relative to the antigen against which they are directed. They are normally formed to counteract exogenous antigens in order to protect the body from substances which have corresponding antigenic determinants. If the immune system of the body incorrectly recognises certain endogenous cells or cell structures as being exogenous, however, antibodies can also be formed against antigenic determinants of endogenous elements. Such endogenous elements are then designated as autoantigens, and the antibodies formed to counteract them are designated as autoantibodies.

Known assay methods for antibodies realise, in one form or another, various basic principles, two of which are shown schematically, for example, at the top of column 3 of U.S. Pat. No. B1 3,654,090. According to a variant which corresponds to the classical radioimmunoassay (RIA), a deficiency of an immobilised antigen is used, and a labelled form of the antibody to be determined is added in a known amount to the sample to be investigated. Information about the presence or concentration of the required antibody can be obtained from the degree of binding of the labelled antibody to the immobilised antigen. The antigen is required in highly pure form for this test based on the competition principle.

According to a second principle, a known amount of the antibody to be determined or of a suitable derivative thereof is immobilised on a solid substrate, and the antibody present in the sample to be investigated and the immobilised antibody are then allowed to compete for a labelled antigen added to the reaction system. The presence or amount of the antibody to be determined is obtained from the reduction in the binding of the labelled antigen to the immobilised antibody and therefore to the solid phase.

In the last-mentioned method of determination, a labelled form of the associated highly pure antigen is required, and the antibody to be determined and the immobilised antibody must be present in amounts such that effective competition can occur between the immobilised antibody and the antibody in the sample to be investigated, the fact that affinities to the labelled antigen may not be completely identical being taken into account.

According to a further principle, in a procedure analogous to the sandwich test well known for antigen determination an excess of an antigen, usually in immobilised form, is first taken, by means of which the total amount of the antibody to be determined is bound, and, by a subsequent second immunological reaction with a second labelled "antigen", against the antibody bound in the first step, the latter is labelled with formation of a sandwich-like immune complex. The second "antigen" is frequently an anti-antibody (double antibody method), or it is used for labelling the labelled so-called protein A, a protein which is obtained from bacteria and binds unspecifically to many IgG antibodies. In this method, the amounts of antigen required are such that the binding capacity is sufficient for binding all antibodies present in the sample. If larger amounts of the antibodies to be determined are expected, the samples must therefore generally be highly diluted before they can be used in the test. This applies in particular to the coated tube technique, which is often preferred for practical reasons, and the microtitre plate technique, in which an antigen-coated test tube has a binding capacity of only about 1–2 µg of human antibodies.

In the determination of antibodies against exogenous antigens, the requirements for the functioning of the various tests can frequently be met without great difficulties. The antibody concentrations against exogenous antigens are normally relatively low, and the associated antigens or haptens can frequently be synthesised in sufficient amounts by a chemical or biotechnological method or can be isolated from natural material and concentrated.

However, if it is intended to determine autoantibodies by one of the principles described, a number of difficulties, some of them considerable, are encountered, both as a result of the autoantibody concentrations which occur and as a result of the nature of the autoantigens.

The determination of autoantibodies is very important for detecting the presence of an autoimmune disease, in particular for correctly interpreting the observed symptoms and avoiding harmful incorrect treatments. Known autoimmune diseases, some of which are extremely severe, are for example rheumatoid arthritis, diabetes mellitus type 1, myasthenia gravis and some autoimmune diseases associated with the thyroid, such as Basedow's hyperthyreosis (also referred to as Graves' disease), anaemic myxoedema and Hashimoto's thyroiditis. In the case of the thyroid autoimmune diseases, thyroglobulin, THS receptor and/or thyroid peroxidase (TPO) act as autoantigens, depending on the type of disease, and recent discoveries have shown that the latter is identical to the so-called microsomal antigen. The present invention is described below in particular with respect to the determination of thyroid autoantibodies, in particular of antibodies against hTPO, but the novel principle on which the invention is based is not restricted to these specific determinations but can also usefully be applied to the determination of other autoantibodies. In the determination of other antibodies, it may in specific cases also have advantages over the assay methods based on the known principles.

Reviews of the current state of knowledge in the area of the thyroid autoimmune diseases are to be found in the scientific literature, for example in the article by Marian Ludgate and Gilbert Vassart in: Autoimmunity, 1990, Volume 7, pages 201–211; in the Review by Jadwiga Furmaniak and Bernard Rees Smith in: Autoimmunity, 1990, Volume 7, pages 63–80; and in the article by P.-M. Schumm-Drager, H. J. C. Wenisch in: Akt. Endokr. Stoffw. 10 (1989), pages 9–102 (special edition), where an overview of the methods for the detection of thyroid autoantibodies is given.

The immunodiagnostic determination of thyroid autoantibodies or autoantibodies generally with corresponding use of one of the determination types mentioned at the outset encounters the fundamental difficulty that the autoantibodies are very frequently directed against autoantigens which are anchored in the cell membrane and are difficult to obtain in the high purity and amount required for the usual procedure. In the case of the human thyroid peroxidase (hTPO), an enzyme which, as an autoantigen, is responsible for Hashimoto's thyroiditis, it is, for example, a glycosylated haemoprotein which is bound to the thyroid membranes. Its antigenic properties, including the types of epitopes present on its surface, are described in the article by P. Carayon et al. in: Endocrinology, Vol. 125, No. 3, pages 1211 to 1218. In order to have this thyroid peroxidase available in sufficient purity and amount as an antigen for the immunodiagnostic determination method based on the known principles, the thyroid peroxidase must be removed from the membrane by a proteolytic method or with the aid of detergents and purified via immune adsorbents or by means of conventional chromatography methods over various separation stages, for example by means of gel filtration, ion exchange chromatography, chromatography via hydrophobic interactions, chromatography via aromatic interactions, adsorption chromatography and chromatography using concanavalin A. These methods are complicated and entail the risk of unintentional changes in the enzyme to be isolated and high material loss. Highly purified natural thyroid peroxidase (TPO) is therefore available only in small amounts and at high prices. As an alternative to isolating the thyroid peroxidase from thyroid glands, attempts were therefore also be made and methods developed to permit the production of TPO by genetic engineering. However, the TPO obtained in this manner is also available only in limited amounts and at high prices, and the identity of the material obtained by genetic engineering with the natural thyroid peroxidase, particularly with regard to the antigenic properties, is not guaranteed in every case.

A further difficulty also arises from the fact that the antigenic properties of the TPO can be very greatly impaired by chemical effects, particularly if, as a result, the three-dimensional structure is changed and/or the disulphide bridges are broken (cf. the stated article by P. Carayon). However, in order to be able to use TPO as a labelled antigen in the classical method for antibody assay, a label must be chemically bonded to the TPO. In addition to the difficulty of obtaining pure TPO, there is at this stage the risk that, as a result of the reactions associated with the labelling, the antigenic properties of the TPO will be influenced so that it no longer corresponds to the natural TPO and is therefore suitable only to a limited extent as an antigen for the detection of autoantibodies. For example, the changes caused by the isolation and/or labelling of the TPO may result in only some of the polyclonal TPO autoantibodes reacting with a TPO labelled in this way.

To avoid at least some of the problems associated with the isolation and labelling of TPO, a test in which a TPO which is not highly purified but used in crude form is employed as an immobilised antigen was developed as a modification of the sandwich test described at the outset for the assay of antibodies. In this test, however, there is the danger that the immobilised crude TPO may also contain other substances having antigenic properties which lead to immobilisation of antibodies other than the required antibodies, and that these will then be labelled in the subsequent, relatively unspecific labelling by a double antibody method or by labelled protein A and will give false positive results.

From practical points of view, in particular with regard to the required work and the achievable accuracy of determination, a further problem in the determination of autoantibodies is that, when an autoimmune disease is present, they occur in extremely large amounts in the biological fluids, particularly the patients' sera. For example, up to 20 µg of human autoantibodies are to be expected in a sample volume of 20 µl of serum. In order to be able to determine them, particularly by the coated tube technique or microtitre plate technique, it is therefore normally necessary to dilute the patients' sera several-fold, which is labour-intensive and time-consuming and constitutes an additional source of error.

In view of the difficulties described in the determination of autoantibodies by the known immunodiagnostic assay methods, there is therefore an urgent need for a novel method for the immunodiagnostic determination of autoantibodies in biological fluids which permits a safe qualitative determination of antibodies in biological fluids, which, as a result of suitable calibration and optimisation of the parameters of the method, is also suitable for the reliable quantitative determination of antibodies, in which undiluted sera can be used and in which it is not necessary to use significant amounts of highly purified antigens for the antibodies to be determined.

It is the object of the present invention to provide such a method.

This object is achieved by an immunological assay method as described in claim 1.

Preferred embodiments are contained in the subclaims.

In the assay method according to the invention, a procedure is adopted in which, for the detection of antibodies (Ak), in particular of autoantibodies, the disturbance of the formation of a sandwich complex of a first immobilised antibody ($Ak_{imm}$), an added antigen (Ag), in particular a crude antigen, and a further antibody (Ak*) which carries a detectable label is determined, said disturbance being due to the presence of the antibodies (Ak) to be determined in the biological fluid. The inhibition of the formation of a sandwich complex of the stated type is evident in a reduction in the binding of the labelled antibody (Ak*) to the solid phase. The disturbance of the formation of the sandwich by the antibody or autoantibody (Ak) to be determined and present in the sample can occur in principle at each individual binding site for the synthesis of the sandwich or at both simultaneously. Substances which act as autoantigens and can be formed against the autoantibodies are, as a rule, complexes of large molecules, generally of a protein nature, which have more than two regions or epitopes involved in the antibody binding, and the antibodies formed are polyclonal. Depending on the choice of the antibodies selected for the test as immobilised or labelled antibodies, it is therefore possible to construct different types of sandwich complexes which—as far as the bonds involved and the disturbance thereof are concerned—may behave very differently with regard to the presence of the autoantibodies (Ak). The construction of such sandwiches with specification of suitable properties for the detection of certain autoantibodies (Ak) can be tailored in particular when both the immobilised antibody ($Ak_{imm}$) and the labelled antibody (Ak*) are suitable monoclonal antibodies. In the case of the determination of autoantibodies with respect to TPO, the epitopes present on this antigen are relatively well characterised, and various monoclonal antibodies are available which are directed against specific epitopes of this antigen. In this connection, reference may be made to the above-mentioned article by P. Carayon et al. in Endocrinology, Volume 125, No. 3, pages 1211–1218.

If such an antibody, in particular a monoclonal antibody, which binds TPO in a region in which autoantibodies against TPO are also bound is chosen as the immobilised antibody against TPO, and if the labelled antibody Ak is chosen so that its binding is not influenced by autoantibodies, the disturbance of the formation of the sandwich is due to competition between the immobilised antibody $Ak_{imm}$ and the antibody Ak to be determined for the complex antigen-labelled antibody (Ag-Ak*), which may be regarded as an indirectly labelled antigen. If the opposite approach is adopted and the immobilised antibodies $Ak_{imm}$ is chosen so that its binding to the antigen is not disturbed by the antibodies (Ak) to be determined, while the labelled antibody Ak* binds to regions or epitopes of the antigen where the antibodies or autoantibodies to be determined also bind, the disturbance of the formation of a sandwich which contains the labelled antibody Ak* takes place owing to the competition between Ak* and Ak for the indirectly immobilised antigen. If both antibodies $Ak_{imm}$ and Ak* bind to those regions of the antigen where the autoantibodies (Ak) also bind, the presence of such autoantibodies (Ak) results in double impairment of the sandwich structure and its immobilisation and hence may give rise to an increase in sensitivity.

A very significant advantage of the method according to the invention is that the antigen Ag need not be present in highly purified form as in the assay methods known to date but can be used as crude antigen, for example in the form of an organ extract. The double antibody specificity which is required for the formation of a sandwich which contains a label means that unspecific disturbances of the test by foreign components which are introduced into the assay together with the crude antigen can be eliminated without difficulties, so that sandwich formation is limited to the required immunological binding partners. While in the case described above, where the crude antigen is immobilised together with accompanying substances, there is the danger that not only antibodes against the immobilised antigen but also immunological binding partners of other antigenic substances present in the crude antigen are bound to the solid phase and labelled, such disturbances are very improbable in the method according to the invention. The possibility of using a crude antigen in the form of a suitable organ extract has the further advantage that it is possible to use relatively gentle recovery methods for the antigen and to dispense with purification steps by means of which the natural structure of the antigen is attacked. The antigen can therefore very much more exactly represent the antigen present in the organism and its complete immunological binding spectrum. The danger that only a fraction of the autoantibodies formed in the organism will be detected by the test is thus smaller.

On the other hand, by a suitable choice of the monoclonal antibodies used for the test, it is also possible to ensure that the test responds very specifically only to certain autoantibodies and can thus be made more selective. If, for example, certain symptoms associated with the autoimmune disease can be attributed to very specific clones of the polyclonal autoantibodies formed by the body, the method for the determination of such autoantibody clones can be made specific by using monoclonal or, optionally, selected polyclonal antibodies.

In the method according to the invention, the expected high autoantibody concentrations present no problem since the crude antigen, for example the crude hTPO, can be used in sufficient amounts comparable with the amounts of autoantibodies without making the test excessively expensive. It has been found that the possibility of using the crude antigen is so advantageous in terms of cost that the two added antibodies ($Ak_{imm}$, Ak*) required in the method according to the invention do not give rise to any cost disadvantage compared with methods operating with highly purified antigens but only one antibody.

The assay method according to the invention is also very suitable for optimisation with regard to the required sensitivity by adapting the intended amounts of antigen Ag or labelled antibody Ak* or immobilised antibody $Ak_{imm}$ in wide limits to the test conditions. This is possible without major problems, owing to the good availability and the relatively low price of the crude, natural antigen used. The amount of antigen can be matched directly with the expected or possible amounts of autoantibody, which also means that the biological fluids, i.e. in particular sera, can be used in undiluted form.

Regarding the amounts of immunological reactants to be used, it is self-evident to one skilled in the art that the amount of added antigen should not be so large that both all antibodies Ak to be determined and all labelled antibodies Ak* or all immobilised antibodies $Ak_{imm}$ are saturated and there is no longer any significant competition between them for the antigen. In such a case, significant formation of an immobilised, labelled sandwich can be suppressed in certain circumstances, and no quantitative conclusions about the actual amounts of autoantibodies present in the sample are possible.

If a deficiency of, for example, labelled antibody Ak* is used relative to the amount of the added antigen, so that only a part of the amount of antigen is labelled with formation of an immune complex Ag-Ak*, the amount of the labelled Ak* must not of course be so small that the amount of complex finally bound is too small owing to its competition with unlabelled antigen for the immobilised antibody $Ak_{imm}$. An analogous situation applies, in another described variant of the method, for the amount of the immobilised antibody $Ak_{imm}$.

The concentrations of antigen Ag, immobilised antibody $Ak_{imm}$ and labelled antibody Ak* which are required or most advantageous for a certain test can be determined, taking into account the expected amounts of the antibodies Ak to be determined, without significant difficulties in routine optimisations by varying the sensitivity of the test (calibration curve) via, for example, the added amounts of antigen.

Antibodies which can be used in the method according to the invention may essentially be all antibodies suitable for immunological assay methods. Their affinity constants are usually in the range from $10^{12}$ to $10^8$ l/mol.

With regard to the solid substrates which can be used for immobilised antibodies $Ak_{imm}$ and the conditions of the immunological reaction (pH between 4 and 9, presence of buffers; temperature in the range from 0° to about 55° C.; reaction times), the procedure does not differ fundamentally from other conventional immunological assay methods. The immunological reaction can be carried out under conditions such that the equilibrium between all reactants is reached; however, it is in principle also possible to stop the reaction at an earlier predetermined time and to determine the ratios at this earlier time.

The method according to the invention is described in detail below with reference to an embodiment which relates to the determination of autoantibodies against human thyroid peroxidase (hTPO) with the use of two added monoclonal antibodies against hTPO and of crude hTPO in the form of an extract from human thyroid glands as added antigen, and its efficiency is compared with that of the known methods for the determination of the same autoantibodies.

In the Figures,

FIG. 1 shows a schematic diagram of the method according to the invention in a first variant in which the immobilised antibody $Ak_{imm}$ binds to a region of the antigen Ag which is also recognised by the antibody Ak which is to be determined and which is preferably an autoantibody, so that the antibody Ak competes with the immobilised antibody $Ak_{imm}$ for the antigen Ag and thus interferes with its fixation on the solid phase; the disturbance caused by the antibody Ak is represented here and in the following FIGS. 2 and 3 symbolically as an intervening movement of the antibody Ak, although, as is quite clear to one skilled in the art, the observed disturbance is due to competition for the antigen.

EXAMPLE

Figure 1:
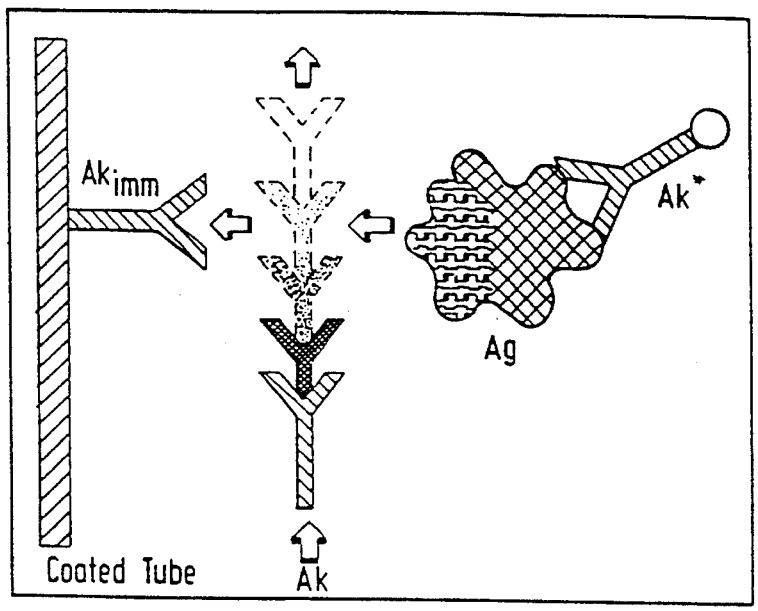
Figure 2:
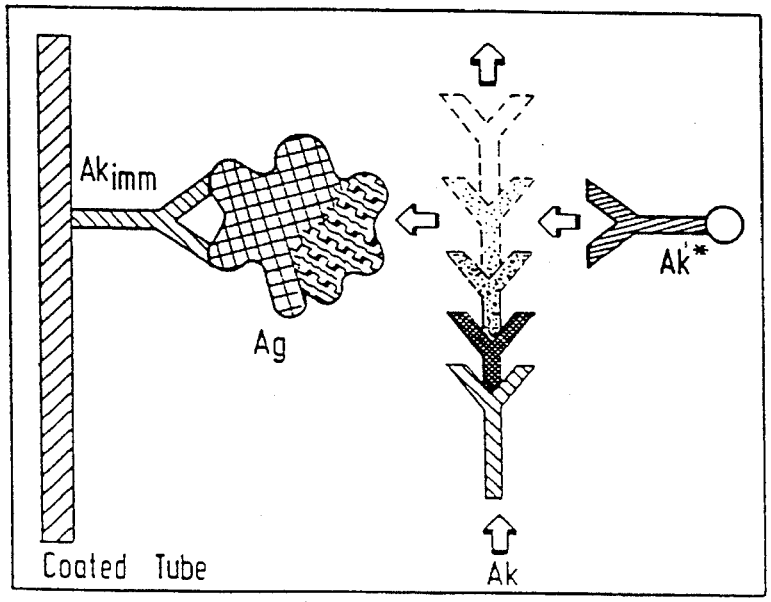
FIG. 2 shows a further variant of the method according to the invention, in which the antibodies Ak to be determined and the labelled antibodies Ak* compete for the region of the antigen Ag which is indirectly immobilised via $Ak_{imm}$ and is recognised by the autoantibody Ak.

The following Example describes the procedure and the practical advantages of an assay in which the method according to the invention is realised, with reference to a preferred embodiment which relates to the detection of human autoantibodies against human thyroid peroxidase (hTPO).

1. Immobilisation of a monoclonal anti-hTPO antibody ($Ak_{imm}$) on a solid phase A purified monoclonal antibody which binds to a region of hTPO which is recognised by human autoantibodies against hTPO was chosen as the antibody which is coupled to the solid phase. The purified monoclonal antibody used was a monoclonal mouse anti-hTPO antibody which had been prepared by the process described in the publication by P. Carayon in: Endocrinology, Vol. 125, No. 3, page 1212, bottom of left column, top of right column, and which was chosen according to the selection criteria described in the same publication so that it recognises hTPO in a region which is also recognised by human anti-hTPO autoantibodies.

The coupling of the stated monoclonal mouse anti-hTPO antibody to the solid phase in the form of the walls of a test tube was carried out by known methods, as follows:

Test tubes (STAR Tubes 12×75 mm from NUNC, catalogue No. 470/319) were each filled with 1 μg of anti-mouse-IgG (SIGMA, catalogue No. MA 8642) in 300 μl of an aqueous buffer solution at pH 7.8, which had a concentration of 10 mmol of TRIS/HCl and 10 mmol of NaCl. After incubation for 20 hours at room temperature, the tubes were washed twice. The tubes were saturated with a solution of 0.5% BSA (bovine serum albumin; SIGMA, catalogue No. A 3294), i.e. the tubes were filled with the saturation solution and incubated for 2 hours at room temperature, after which the content was decanted. In a subsequent third step, the added monoclonal mouse anti-hTPO antibody was bound to the solid phase by immunoextraction from a solution of the stated monoclonal antibody which contained the latter in an amount of 0.2 μg in 300 μl of the above-mentioned buffer solution, incubation being carried out for 20 hours at room temperature for this purpose. Thereafter, the tubes were washed and a final saturation was carried out using the same saturation solution as above. The tubes containing the immobilised monoclonal antibody were then freeze-dried.

2. Preparation of an hTPO extract of human thyroid

Frozen human thyroids (60 g) were comminuted, buffer (200 ml of phosphate-buffered saline solution, PBS) was added and homogenisation was then carried out by means of a homogeniser (Ultraturrax from IKA Werke). Centrifuging was carried out for one hour at 100,000 g, after which the supernatant was removed and the pellet obtained was rehomogenised in the same way as the comminuted thyroids. This was followed by further centrifuging at 100,000 g for 1 hour. The pellet now obtained was again rehomogenised in PBS (200 ml) which additionally contained, as a detergent, 0.5% Triton X 100 from PIERCE (catalogue No. 28314), and stirring was carried out for 1 hour at 4° C. Finally, the homogenate obtained was centrifuged at 100,000 g for 2 hours. The resulting supernatant is the hTPO extract which is used as crude natural antigen Ag in the method according to the invention for the determination of autoantibodies against hTPO.

3. Preparation of an anti-hTPO antibody (Ak*) labelled with a chemiluminescent label A monoclonal mouse anti-hTPO antibody which was obtained in principle by the same method as the corresponding monoclonal antibody described above under 1. but which was chosen so that it binds hTPO outside the region which is also recognised by human autoantibodies against hTPO is labelled with acridinium ester by known methods. For this purpose, the pure monoclonal antibody (100 μg in 100 μl of PBS) is reacted with acridinium ester (2 μg in 2 μl of acetonitrile) for 10 min at room temperature. The antibody labelled with the acridinium ester is then separated from unreacted free acridinium ester by HPLC.

4. Determination of human autoantibodies against hTPO a) For the determination of human autoantibodies against hTPO, in the present case the labelled antibody Ak* was first reacted, in a molar ratio of 1:1, with the hTPO extract used as antigen Ag. The reaction was carried out in the course of 20 hours at 4° C. in a buffer which contained the following components in the concentrations stated below: 50 mmol of sodium phosphate, 0.1% by weight of Triton X 100, 0.2% by weight of EDTA, 0.3% of BSA (bovine serum albumin), 100 μg/ml of mouse IgG (SIGMA, No. I 5381) and 10 μg/ml of bovine IgG (SIGMA, No. 5506). The pH of the buffer was 7.8.

b) For the detection of human autoantibodies against hTPO or for the calibration, the following procedure was used in each case:
1. 20 μl of the sample to be investigated or of the standard or serum were pipetted into test tubes which had been coated with mouse anti-hTPO antibodies by the process step described under 1.
2. 300 μl of the cocktail prepared according to 4a) and containing the antigen hTPO in the form of the extract from human thyroids and the labelled mouse anti-hTPO antibody reacted therewith were then pipetted.
3. After the end of the addition, the reaction mixture obtained was incubated for 3 hours at room temperature while shaking. The test tubes were then washed, and the amount of the acridinium ester tracer bound to the wall of the test tube was measured in a Berthold Autoclinilumat LB 952/16 in a manner known per se by means of the light reaction.

Figure 4:
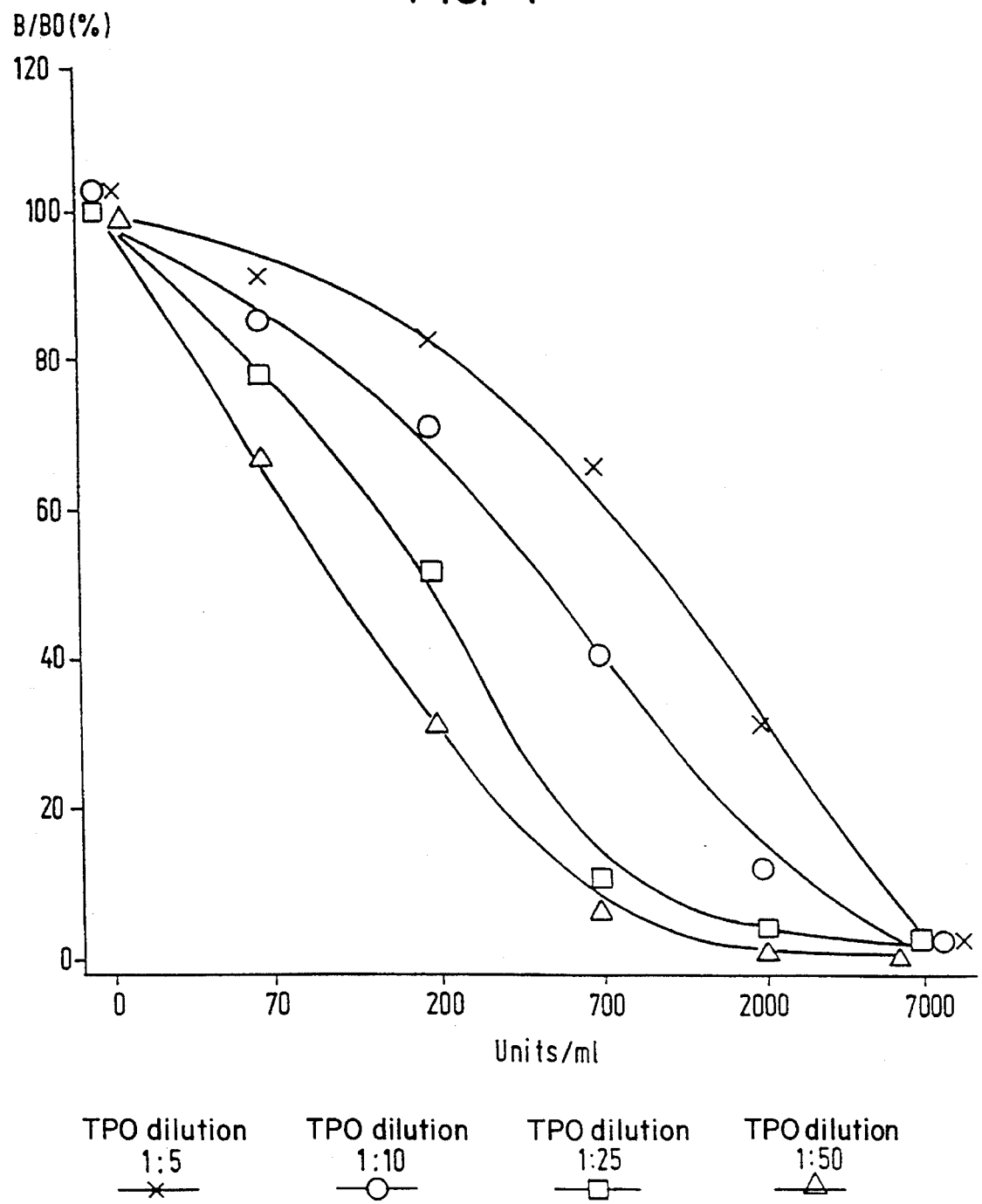
FIG. 4 shows a graphic representation of the standard curve in an assay for the detection of human autoantibodies against human thyroid peroxidase (hTPO) as a function of the amount of antigen used (crude hTPO).

FIG. 4 shows the measured curves obtained for various amounts of autoantibodies in the sample to be investigated or in the standard used, for assays with different amounts of added antigen (hTPO) in the form of a human thyroid extract, the "TPO dilution" data relating to the thyroid membrane extract described above under 2. FIG. 4 clearly shows that the shape of the curve and hence the measurement sensitivity can be varied by varying the amount of antigen used (amount of hTPO).

5. Clinical data

In a clinical study, the results obtained with the novel method described were compared with those obtained using existing immunological assay methods for the determination of autoantibodies against hTPO for 29 positively reacting patients.

The results are summarised in Table 1.

TABLE 1

| Standard group Patient pool (N = 25) Patient No. | Autoantibodies units/ml | | | |
|---|---|---|---|---|
| | a)* all neg. | b)* all neg. | c)* all neg. | d) Novel method all neg. |
| 1 | 156 | neg. | 168 | 138 |
| 2 | neg. | neg. | neg. | neg. |
| 3 | 129 | 83 | 240 | 207 |
| 4 | 3869 | 1163 | 8706 | 3742 |
| 5 | 2225 | 1414 | 2163 | 2235 |
| 6 | 182 | 91 | 249 | 147 |
| 7 | 198 | 598 | 2596 | 1728 |
| 8 | 3232 | 1006 | 5283 | 4834 |
| 9 | 1015 | 110 | 362 | 784 |
| 10 | neg. | neg. | 110 | neg. |
| 11 | 433 | 198 | 886 | 600 |
| 12 | 1049 | 359 | 1171 | 1473 |
| 13 | 140 | 89 | 168 | 135 |
| 14 | neg. | neg. | neg. | neg. |
| 15 | 134 | 86 | 255 | 94 |
| 16 | 2768 | 7496 | 5106 | 5159 |
| 17 | 2154 | 1412 | 4090 | 2791 |
| 18 | 341 | 105 | neg. | 109 |
| 19 | 898 | 530 | 1173 | 1552 |
| 20 | 1478 | 476 | 1125 | 1471 |
| 21 | 3753 | 2215 | 2593 | 5069 |
| 22 | 274 | 108 | 141 | 237 |
| 23 | 784 | 516 | 461 | 414 |
| 24 | 921 | 472 | 521 | 451 |
| 25 | 405 | 341 | 798 | 709 |
| 26 | 1415 | 424 | 997 | 1032 |
| 27 | 1914 | 1011 | 2608 | 2170 |
| 28 | 183 | 704 | 2631 | 1747 |
| 29 | 161 | neg. | 130 | 378 |

*Results of comparative methods

In this Table 1, columns a), b) and c) relate to the results of assay methods of the prior art which are explained in more detail below, while d) shows the results obtained by the novel method carried out as described above.

The methods of the prior art which were used as comparative methods and compared with the method according to the invention were specifically:

a) A method in which an anti-hTPO antibody on the solid phase is used. Radiolabelled and purified hTPO is displaced from the solid phase by human autoantibodies. The test used is a commercial test which is commercially available from Henning Berlin GmbH Chemie as DYNOtest Anti-TPO.

B) In this test, protein A is immobilised on the solid phase. Antibodies in a sample are detected by their binding to the solid phase and their subsequent detection with the aid of labelled purified hTPO. In a specific case, radioiodine-labelled hTPO is used in the (Henning Berlin GmbH Chemie)'s IMMUtest Anti-TPO.

c) In this test, crude TPO (as so-called microsomal antigen) is used in immobilised form on the solid phase. The binding and the detection of the bound autoantibodies are carried out with the aid of a labelled protein A. The comparative test is the from Henning Berlin GmbH Chemie PROMAK assay.

Table 1 with the comparative results clearly shows that comparative method a) (purified labelled hTPO as tracer) and comparative method b) (protein A on a solid phase, purified labelled hTPO as tracer) in some cases give lower values than the assay method according to c) and method d) according to the invention. Thus, assay method a) gives substantially lower values than the other methods for individual patient samples (patients 7, 16, 28), while assay method b) gives negative results for certain patients which are slightly positive in the other methods (patients 1, 29) or gives lower values for certain patients than in the other assay methods (patients 4, 8, 11, 12, 17, 19, 20, 27). It should be pointed out that, in the case of patients 1 and 29, the samples were even determined incorrectly as being autoantibody-free by assay method b). In the case of patients 7 and 28, assay method a) finds the patients only extremely slightly positive, whereas they are strongly positive in the other methods.

Method c) has the disadvantage that, in addition to antibodies against hTPO, a large number of other autoantibodies against accompanying proteins are also measured, which leads, for example, to autoantibodies against hTPO being detected for patient 10, who is free from autoantibodies against hTPO according to all other methods.

The principle on which the method according to the invention is based is variable in many respects, as explained in detail at the outset. Since an antibody is labelled, any currently known label can be used for labelling. Instead of the preceding reaction of antigen (crude hTPO) with the labelled antibody as described in the specific case, it is also possible to carry out the method as a synchronous reaction, i.e. instead of the crude antigen (hTPO) being indirectly prelabelled with the labelled antibody in a separate step prior to the addition of the sample to be investigated, the incubation is carried out as follows:

The sample to be investigated for autoantibodies is first pipetted into the test tube coated with the immobilised antibody, the labelled antibody Ak* is then added and finally the antigen solution (hTPO solution) is added, with the result that the reaction is started.

Figure 3:
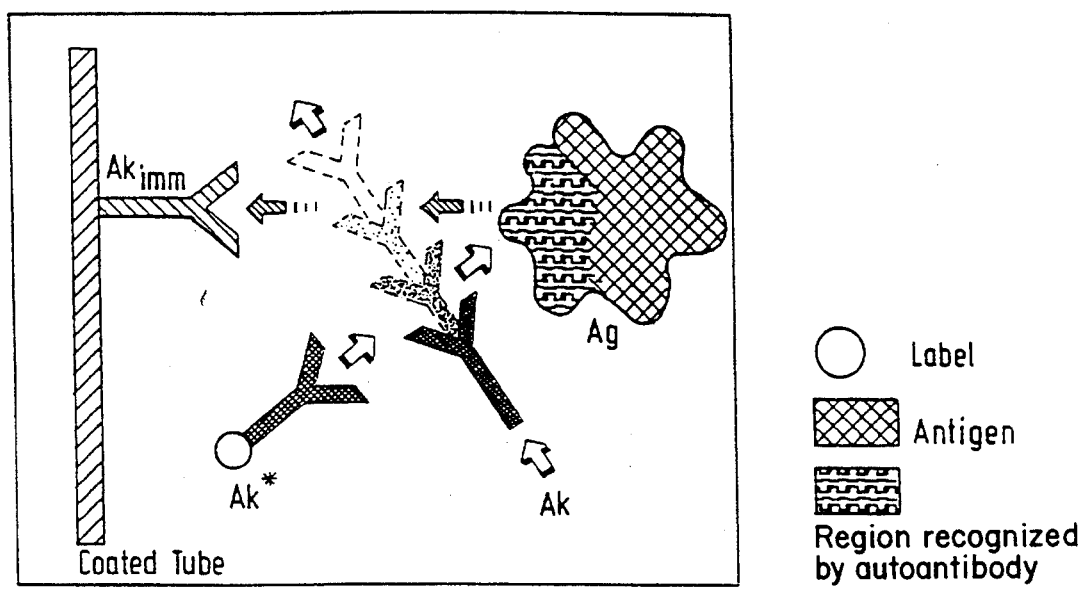
FIG. 3 shows a third variant of the method according to the invention in which both the immobilised antibody $Ak_{imm}$ and the labelled antibody Ak* bind to a region of the antigen Ag which is also recognised by the autobody Ak, so that the presence of the antibody Ak in the sample causes a double disturbance.

Such a procedure is advantageous when the binding conditions are such that human autoantibodies also influence and weaken the interaction between the labelled antibody Ak* and the antigen Ag (hTPO), similarly to the scheme according to FIG. 3.

Other pipetting schemes are also possible. For example, it is also possible not to immobilise the first antibody $Ak_{imm}$ until during the assay procedure by placing a solid phase with a binder for $Ak_{imm}$ in the test vessel and then pipetting in, for example, a mixture of $Ak_{imm}$ and Ak* and finally starting the reaction by adding antigen Ag.

Although the lack of the necessity to predilute the samples is an important advantage of the method according to the invention, it is of course also possible, where required, to vary the test so that the samples are used in prediluted form.

As already mentioned at the outset, the novel principle of the method is not restricted to the determination of autoantibodies against hTPO. Similar advantages are also expected for the determination of other autoantibodies which are formed against membrane-associated and other autoantigens. In this context, it is possible to mention the determination of autoantibodies against acetylcholine receptors of the nicotine type, the occurrence of which is generally believed to be characteristic of the severe autoimmune disease myasthenia gravis.

However, the method according to the invention can of course also be used for the determination of antibodies which are not autoantibodies and may occur in the biological fluids in very much lower concentrations than autoantibodies. Here too, the method according to the invention can in individual cases have the advantage that antigens obtainable in pure form only with difficulty can be used in crude form and/or that direct labelling of antigens which are sensitive and/or difficult to label can be avoided.

I claim:

1. An immunological assay method for the determination of autoantibodies in a biological fluid obtained from a subject suspected of suffering from an autoimmune disease, the presence of such autoantibodies being indicative of the autoimmune disease, the method comprising the steps of:

incubating said biological fluid for a predetermined time period under conditions favoring specific binding of antibodies to antigens with a predetermined amount of an antigen in the form of a crude extract from a human or animal organ wherein said antigen has at least a first binding site and a second binding site, a solid phase or microsolid phase bearing a predetermined amount of a first immobilized antibody which specifically binds to said first binding site of said antigen, and a predetermined amount of a further antibody which bears a detectable label and specifically binds to said second binding site of said antigen;

wherein autoantibodies present in said biological fluid prevent, by competitive inhibition, specific binding of said first immobilized antibody to said first binding site, and specific binding of said further antibody to said second binding site;

separating said solid phase or microsolid phase bearing said first immobilized antibody from non-immobilized material; and determining the presence of or amount of said detectable label in said solid phase or microsolid phase bearing said first immobilized antibody; and inversely correlating the presence of or amount of detectable label in said solid phase or microsolid phase with the presence of or amount of the autoantibodies to be detected in the biological fluid.

2. The method of claim 1, wherein at least one of said first immobilized antibody or said further antibody is a monoclonal antibody.

3. The method of claim 1, wherein both of said first immobilized antibody and said further antibody are monoclonal antibodies.

4. The method of claim 1, wherein said solid phase is a vessel coated with said first immobilized antibody.

5. The method of claim 1, wherein said detectable label is selected from the group consisting of a radioactive isotope, an enzyme, a fluorescent label, a chemiluminescent label, and a substrate for an enzymatic detection reaction.

6. The method of claim 1, wherein at least one of said first immobilized antibody or said further antibody is a polyclonal antibody.

7. An immunological assay method for the determination of autoantibodies to thyroid peroxidase in a biological fluid obtained from a subject suspected of suffering from an autoimmune disease, the presence of such autoantibodies being indicative of the autoimmune disease, the method comprising the steps of:

incubating said biological fluid for a predetermined time period under conditions favoring specific binding of antibodies to antigens with a predetermined amount of an antigen in the form of a crude extract from human or animal thyroids wherein the antigen has at least a first binding site and a second binding site, a solid phase or microsolid phase bearing a predetermined amount of a first immobilized antibody which specifically binds to said first binding site of said antigen, and a predetermined amount of a further antibody which bears a detectable label and specifically binds to said second binding site of said antigen;

wherein autoantibodies present in said biological fluid prevent, by competitive inhibition, specific binding of said first immobilized antibody to said first binding site, and specific binding of said further antibody to said second binding site;

separating said solid phase or microsolid phase from non-immobilized material;

determining the presence of or amount of said detectable label in said solid phase or microsolid phase; and inversely correlating the presence of or amount of detectable label in said solid phase or microsolid phase with the presence of or amount of the autoantibodies to be detected in the biological fluid.

8. The method of claim 7, wherein at least one of said first immobilized antibody or said further antibody is a monoclonal antibody.

9. The method of claim 7, wherein both of said first immobilized antibody and said further antibody are monoclonal antibodies.

10. The method of claim 7, wherein said solid phase is a vessel coated with said first immobilized antibody.

11. The method of claim 7, wherein said detectable label is selected from the group consisting of a radioactive isotope, an enzyme, a fluorescent label, a chemiluminescent label, and a substrate for an enzymatic detection reaction.

12. The method of claim 7, wherein at least one of said first immobilized antibody or said further antibody is a polyclonal antibody.

* * * * *

UNITED STATES PATENT AND TRADEMARK OFFICE
CERTIFICATE OF CORRECTION

PATENT NO. : 5,501,955
DATED : March 26, 1996
INVENTOR(S) : BERGMANN

It is certified that errors appear in the above-identified patent and that said Letters Patent is hereby corrected as shown below:

On the title page:

item [75]    Andreas Bergmann, Berlin, Germany
item [19] should read --Bergmann--

Please correct item [73] On the title page as follows:

[73]    Assignee:  B.R.A.H.M.S Diagnostica GmbH,
                      Berlin, Germany Signed and Sealed this Seventeenth Day of December, 1996

Attest:

BRUCE LEHMAN

Attesting Officer                Commissioner of Patents and Trademarks